(12) United States Patent
Sasatsu et al.

(10) Patent No.: US 7,090,997 B2
(45) Date of Patent: Aug. 15, 2006

(54) DIAGNOSTIC AGENT AND TEST METHOD FOR COLON CANCER USING TANNASE AS INDEX

(75) Inventors: Masanori Sasatsu, Hino (JP); Masahisa Noguchi, Hachioji (JP); Taisei Shiratori, Misato (JP)

(73) Assignee: Eisai Co., Ltd., Tokyo (JP)

( * ) Notice: Subject to any disclaimer, the term of this patent is extended or adjusted under 35 U.S.C. 154(b) by 433 days.

(21) Appl. No.: 10/415,503

(22) PCT Filed: Oct. 26, 2001

(86) PCT No.: PCT/JP01/09449

§ 371 (c)(1),
(2), (4) Date: Apr. 28, 2003

(87) PCT Pub. No.: WO02/34938

PCT Pub. Date: May 2, 2002

(65) Prior Publication Data

US 2004/0137549 A1    Jul. 15, 2004

(30) Foreign Application Priority Data

Oct. 26, 2000    (JP) .............................. 2000-326839

(51) Int. Cl.
*C12Q 1/14*    (2006.01)
*A61B 5/00*    (2006.01)
*C12R 1/44*    (2006.01)
*C12N 1/20*    (2006.01)
*C12N 9/18*    (2006.01)
*C12Q 1/44*    (2006.01)

(52) U.S. Cl. ............................ 435/36; 435/19; 435/882; 435/887; 436/64

(58) Field of Classification Search ............... None
See application file for complete search history.

(56) References Cited

U.S. PATENT DOCUMENTS 5,552,292 A    9/1996    Uchida et al. ............. 435/7.23

FOREIGN PATENT DOCUMENTS

| JP | 10-132822 | 5/1998 |
|---|---|---|
| WO | WO 98/05960 | 2/1998 |

OTHER PUBLICATIONS

Ahme S, Nobaek S, Jeppsson B, Adlerberth I, Wold AE, Molin G (1998) 85, 88 (Abstract Only).*
Berg RD (1996) Trends Microbiol. 4, 430-435.*
Fervenza FC, Contreras GE, Garratt KN, Steckelberg JM (1999) Mayo Clin Proc 74, 1227 (Abstract only).*
Finegold SM, Sutter VL, Sugihara PT, Elder HA, Lehmann SM, Phillips RL (1977) Am J Clin Nutr 30, 1781 (Abstract only).*
Herchline TE, Ayers LW (1991) J Clin Nicrobiol. 29, 419-421.*
Johansson ML, Nobaek S, Berggren A, Nyman M, Bjorck I, Ahrne S, Jeppsson B, Molin G (1998) Int J Food Microbiol 42, 29 (Abstract Only).*
Lessing MP, Crook DW, Bowler IC, Gribbin B (1996) QJM 89, 855 (Abstract only).*
Mandel JS, Church TR, Ederer F, Bond JH (1999) J. Nat Can. Inst. 91, 434-437.*
Moore WEC & Moore LH (1995) Appl. & Env. Microbiol. 61, 3202-3207.*
Nelson KE, Thonney ML, Woolston TK, Zinder SH, Pell AN (1998) Appl. Env. Micro. 64, 3824-3830.*
Osawa R, Walsh TP (1993) Appl. Env. Micro. 59, 1251-1252.*
Song Y, Kato N, Liu C, Matsumiya Y, Kato K, Watanabe K (2000) FEBS Microbiol. Lett. 187, 167 (Abstract only).*
Krein, et al., "Association of *Streptococcus bovis* with carcinoma of the colon", *The New England Journal of Medicine*, 297: 800-802 (1977).
Henderson et al., Case Report; "*Streptococcus bovis* endocarditis and carcinoma of the colon", *British Journal of Hospital Medicine*, 41:85 (1989).
Darjee and Gibb, "Serological investigation into the association between *Streptococcus bovis* and colonic cancer", *Journal of Clinical Pathology*, 46: 1116-1119 (1993).
Copeland and Malster, "The association between *Streptococcus bovis* endocarditis and carcinoma of the colon", *Postgraduate Medical Journal*, 69: 241 (1993).
Cherukuri et al., "*Streptococcus bovis* endocarditis and colonic carcinoma", *Irish Medical Journal*, 87(5): 154 (1994).
Goumas et al., "Lateral neck abscess caused by *Streptococcus bovis* in patient with undiagnosed colon caner", *The Journal of Laryngology and Otology*, 111: 666-668 (1997).
Osawa et al., "*Streptococcus gallolyticus* sp. *nov.*; Gallate degrading organisms formerly assigned to *Streptococcus bovis* ", *Systematic and Applied Microbiology*, 18: 74-78 (1995).
Osawa et al., "Isolation of tannin-degrading lactobacilli from humans and fermented food", *Applied and Environmental Microbiology*, 66(7): 3093-3097 (2000).
Oakey, et al. "Enzyme Production by Lactobacilli and the Potential Link with Infective Encocarditis." *Journal of Applied Bacteriology*. vol. 78, pp. 142-148, 1995.
Osawa. "Formation of a Clear Zone on Tannin-Treated Brain Heart Infusion Agar by a *Streptococcus* sp. Isolated from Feces of Koalas." *Applied and Environmental Microbiology*, pp. 829-831, 1990.

* cited by examiner

*Primary Examiner*—Terry McKelvey
*Assistant Examiner*—Christopher Bull
(74) *Attorney, Agent, or Firm*—Choate, Hall & Stewart, LLP

(57) ABSTRACT

A diagnostic agent for colon cancer, which comprises a reagent for detecting a tannase high-producing bacterium or measuring an amount of tannase contained in an intracolonic microflora sample, and a test method for colon cancer, which comprises the step of detecting a tannase high-producing bacterium or measuring an amount of tannase contained in an intracolonic microflora sample.

1 Claim, 2 Drawing Sheets

SEQUENCE LISTING

```
<160> NUMBER OF SEQ ID NOS: 1

<210> SEQ ID NO 1
<211> LENGTH: 1490
<212> TYPE: RNA
<213> ORGANISM: Staphylococcus lugdunensis

<400> SEQUENCE: 1
uuagaguuug aucauggcuc aggaugaacg cuggcggcgu gccuaauaca ugcaagucga      60
gcgaacagau aaggagcuug cuccuuugac guuagcggcg gacgggugag uaacacgugg     120
```

-continued

```
guaaccuacc uauaagacug ggacaacuuc gggaaaccgg agcuaauacc ggauaauaug    180
uugaaccgca ugguucaaua gugaaagaug guuuugcuau cacuuauaga uggacccgcg    240
ccguauuagc uaguugguga gguaacggcu caccaaggca acgauacgua gccgaccuga    300
gagggugauc ggccacacug gaacugagac acgguccaga cuccuacggg aggcagcagu    360
agggaaucuu ccgcaauggg cgaaagccug acggagcaac gccgcgugag ugaugaaggu    420
cuuaggaucg uaaaacucug uuauuaggga agaacaaacg uguaaguaac ugugcacguc    480
uugacgguac cuaaucagaa agccacggcu aacuacgugc cagcagccgc gguaauacgu    540 aggugcaag cguuauccgg aauuauuggg cguaaagcgc gcguaggcgg uuuuuuaagu    600
cugaugugaa agcccacggc ucaaccgugg agggucauug gaaacuggaa aacuugagug    660
cagaagagga aaguggaauu ccaugcuguag cggugaaaug cgcagagaua uggaggaaca    720
ccaguggcga aggcgacuuu cuggucugua acugacgcug augugcgaaa gcgugggggau    780 caaacaggau uagauacccu gguaguccac gccguaaacg augagugcua aguguuaggg    840
gguuuccgcc ccuuagugcu gcagcuaacg cauuaagcac uccgccuggg gaguacgacc    900
gcaagguuga aacucaaagg aauugacggg gacccgcaca agcggugagg caugugguuu    960
aauucgaagc aacgcgaaga accuuaccaa aucuugacau ccuuugaccg cucuagagau   1020
agagucuucc ccuucggggg acaaagugac aggugguggca ugguugucgu cagcucgugu   1080
cgugagaugu uggguuaagu cccgcaacga gcgcaacccu uaagcuuagu ugccaucauu   1140
uaguugggca cucuaaguug acugccggug acaaaccgga ggaagguggg gaugacguca   1200
aaucaucaug ccccuuauga uuugggcuac acacgugcua caauggacaa uacaaagggc   1260
agcgaaaccg cgaggucaag caaaucccau aaaguuguuc ucaguucgga uuguagucug   1320
caacucgacu acaugaagcu ggaaucgcua guaaucguag aucagcaugc uacggugaau   1380
acguucccgg gucuuguaca caccgcccgu cacaccacga gaguuuguaa cuacccgaag   1440
ccgguggagu aaccauucgg agcuagccgu cgaaggugga cuaagauggu          1490
```

DIAGNOSTIC AGENT AND TEST METHOD FOR COLON CANCER USING TANNASE AS INDEX

TECHNICAL FIELD

The present invention relates to a diagnostic agent for colon cancer and a test method for colon cancer.

BACKGROUND ART

In recent years, morbidity of colon cancer is increasing with the westernization of diets in Japan. It is said that high-fat diets and low-fiber diets change the intestinal microflora and increase production of carcinogens, and further, reduction of feces amount prolongs intestinal feces retention time and hence prolongs contact time between carcinogens and the intestinal canal, resulting in increase of risks of oncogenesis. Bacteria in the intestine extremely closely relate to health and diseases of hosts and considered to associate with colon cancer through diet components and body components.

*Streptococcus* (*St..*) *bovis* is known as a pathogenic bacterium of infectious endocarditis, and high concurrent incidence of infectious endocarditis due to this bacterium and colon cancer attracts attention in Europe and United States (Honberg P. Z. et al., Lancet, i: 163–164, 1987). Meanwhile, Osawa et al. isolated a bacterium having a tannase activity, which hydrolyzes an ester bond in tannic acid to release gallic acid, from feces of koala eating eucalyptus containing tannin at a high concentration, and identified this bacterium as *St. bovis* biotype I (Osawa R. et al., Appl. Environ. Microbiol., 56: 829–831, 1990). This bacterium has the tannase activity for degrading tannin to release gallic acid, and contains decarboxylase that decarboxylates gallic acid into pyrogallol, and it is proposed that it should be newly designated as *St. gallolyticus*. Osawa inferred a possibility that this *St. gallolyticus* was a bacterium identical to *St. bovis* isolated from a colon cancer patient concurrently having infectious endocarditis (Osawa R., RIKEN Symposium Abstracts, "Classification and Ecology of Lactic Acid Bacteria", pp. 36–45, 1996).

In general, a substance referred to as tannin belongs to polyphenols, natural substances constituting an important portion of phenolic compounds, and has toxic and growth-inhibitory actions on microorganisms as well as an astringent taste. While various classifications of tannin have been proposed, tannin is largely classified into hydrolysable tannin and condensed tannin for convenience. The former is structurally pyrogallol tannin, and it is also referred to as pathological tannin since it is contained in nutgall or gall nut in a large amount. On the other hand, the latter is catechol tannin, and it is also referred to as physiological tannin since it is a normal component of plants. The hydrolysable tannin has a chemical structure in which phenolic acid (gallic acid, ellagic acid etc.) binds to a saccharide as a core through an ester bond. It is known that this hydrolysable tannin is hydrolyzed by tannase, which is a tannin-degrading enzyme mainly produced by fungi such as *Aspergillus* and *Candida* living in soil. However, production of tannase by bacteria living in the intestinal canal of animals had not been reported before the publication of Osawa.

Since then, it has been reported that *Lonepinella koalarum* was isolated from feces of koala as a tannase-positive bacterium, in addition to *St. gallolyticus*, and also isolated mainly from herbivorous animals (Osawa R., Syst. Appl. Microbiol., 15: 144–147, 1992). Recently, it has been further reported that *Lactobacillus* (*L.*) *plantarum* was isolated from human feces. *L. plantarum* is a lactobacillus mainly isolated from silos, and infectious endocarditis due to *L. plantarum* has also been reported (Oakey H. J. et al., J. Appl. Bacteriol., 78: 142–148, 1995).

The onset mechanism of colon cancer has been studied by many researchers, and existence of active oxygen can be mentioned as a part of the mechanism (Babbs C. F. et al., Free Rad. Biol & Med., 8: 191–200, 1990). Active oxygen exhibits a sterilizing action against microorganisms entering into a living body to protect the body from infection. On the other hand, active oxygen has a risk of increasing adverse reaction products that can damage body functions by radical chain reactions and thus worsening various pathological conditions. It is considered that balance of production and elimination of active oxygen is lost in, in particular, aging and life habit diseases such as arteriosclerosis and cancer, leading to worsening of conditions over a long time.

Many chemical substances have been discovered as substances producing active oxygen, and gallic acid and pyrogallol are among them (Khan N. S., Mutagenesis, 13: 271–274, 1998).

DISCLOSURE OF THE INVENTION

The inventors of the present invention established a hypothesis about the relationship between bacteria having a tannase activity and colon cancer as follows. When tannase acts on hydrolysable tannin, gallic acid is produced, pyrogallol is further produced in the presence of gallic acid decarboxylase, and thus a chemical substance producing active oxygen is released. If a tannase-positive bacterium is involved in this pathway, active oxygen is produced in the presence of the tannase-positive bacterium, and this would be one of causes of onset of cancer, in particular, colon cancer.

Under such a background, the inventors of the present invention assiduously studied in order to elucidate how a bacterium having a tannase activity in the colon associates with colon cancer. As a result, they found that *Staphylococcus* (*S.*) *lugdunensis*, a tannase-positive bacterium, was found only in colon cancer patients, and, further found that *S. lugdunensis* produced a larger amount of tannase in comparison with other tannase-positive bacteria. Accordingly, it is considered that a large amount of tannase produced by *S. lugdunensis* causes colon cancer, and that a part of colon cancer cases can be diagnosed or tested by detecting a tannase high-producing bacterium or tannase.

The present invention was accomplished based on the aforementioned findings and provides the following.

(1) A diagnostic agent for colon cancer, which comprises a reagent for detecting a tannase high-producing bacterium contained in an intracolonic microflora sample.

(2) A diagnostic agent for colon cancer, which comprises a reagent for detecting *Staphylococcus lugdunensis* contained in an intracolonic microflora sample.

(3) A test method for colon cancer, which comprises the step of detecting a tannase high-producing bacterium contained in an intracolonic microflora sample.

(4) A test method for colon cancer, which comprises the step of detecting *Staphylococcus lugdunensis* contained in an intracolonic microflora sample.

(5) A diagnostic agent for colon cancer, which comprises a reagent for measuring an amount of tannase contained in an intracolonic microflora sample.

(6) The diagnostic agent according to (5), wherein the amount of tannase is measured based on an enzymatic activity.
(7) The diagnostic agent according to (5), wherein the amount of tannase is measured by an immunoassay.
(8) A test method for colon cancer, which comprise the step of measuring an amount of tannase contained in an intracolonic microflora sample.
(9) The method according to (8), wherein the amount of tannase is measured based on an enzymatic activity.
(10) The method according to (8), wherein the amount of tannase is measured by an immunoassay.

BEST MODE FOR CARRYING OUT THE INVENTION

Figure 1:
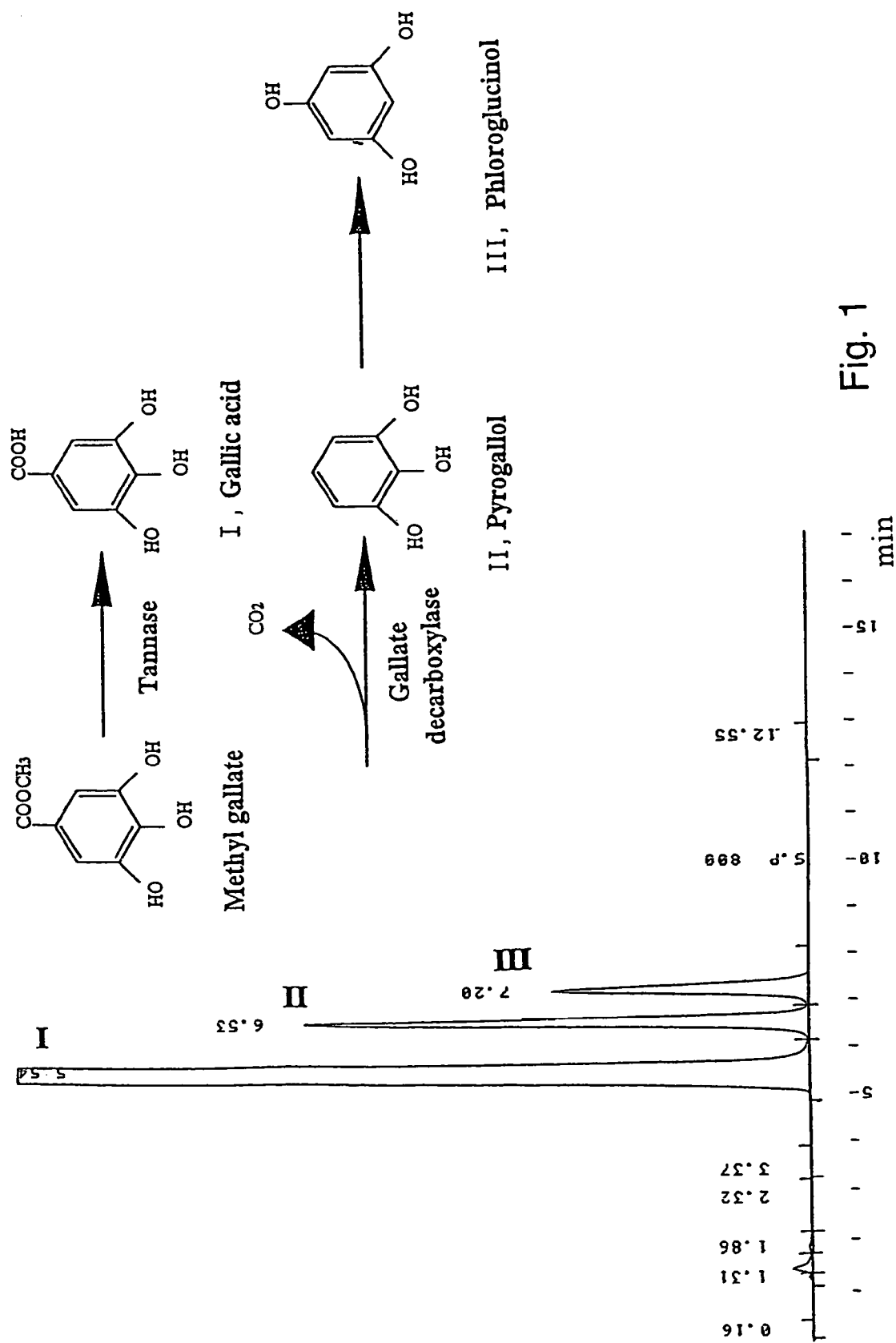
FIG. 1 shows quantification of gallic acid, pyrogallol and phloroglucinol by HPLC.

Hereafter, embodiments of the present invention will be explained in detail.
The present invention provides a diagnostic agent for colon cancer comprising a reagent for detecting a tannase high-producing bacterium contained in an intracolonic microflora sample and a test method for colon cancer comprising the step of detecting a tannase high-producing bacterium contained in an intracolonic microflora sample. The present invention also provides a diagnostic agent for colon cancer comprising a reagent for detecting S. lugdunensis contained in an intracolonic microflora sample and a test method for colon cancer comprising the step of detecting S. lugdunensis contained in an intracolonic microflora sample.
In the present invention, the term "tannase high-producing bacterium" refers to a bacterium producing 0.3 mM or more, preferably 0.5 mM or more, of gallic acid and pyrogallol as a total amount of them as measured by the tannase activity measurement method using HPLC described later in Example 2.
The tannase high-producing bacterium is preferably S. lugdunensis.
S. lugdunensis has a high tannase producing ability and generally satisfies the aforementioned definition of the tannase high-producing bacterium. Hereinafter, for convenience, S. lugdunensis and other tannase high-producing bacteria are generically referred to as a tannase high-producing bacterium.
The expression "intracolonic microflora sample" means a sample containing bacterial flora in the colon, and examples thereof include feces, intestinal canal wash and so forth.
The tannase high-producing bacterium contained in an intracolonic microflora sample can be detected by culturing a bacterium existing in the intracolonic microflora sample for isolation and measuring the tannase producing ability of the bacterium, or identifying the bacterium in the intracolonic microflora sample to determine whether it is a tannase high-producing bacterium or not. In the culture for isolation, the tannase positive bacterium is preferably isolated by using a tannin-treated agar medium. Further, identification of the bacterium is preferably performed after the isolation of the tannase-positive bacterium, because such a procedure facilitates the identification. The bacterium can be identified by searching bacteriological properties such as biochemical properties and/or searching homologies of nucleotide sequences that can be used for identification of bacteria. Examples of the nucleotide sequences that can be used for identification of bacteria include a nucleotide sequence of the 16S-rRNA gene.
Hereafter, the detection method will be specifically explained by using S. lugdunensis as an example.
S. lugdunensis can be detected by isolating a tannase-positive bacterium from an intracolonic microflora sample by using a tannin-treated agar medium, searching various already known biochemical properties for the isolated tannase-positive bacterium, or searching homology of the nucleotide sequence of the 16S-rRNA gene.
Examples of the biochemical properties include various properties such as degrading abilities for glucose, fructose, D-mannose, maltose, lactose, D-trehalose, D-mannose, xylitol, D-melibiose, D-raffinose, D-xylose, sucrose, α-methyl-D-glucoside and N-acetyl-D-glucosamine, ability of reducing nitrate to nitrite, alkaline phosphatase-producing ability, acetylmethylcarbinol-producing ability, arginine hydrase-producing ability, and urease-producing ability, and the biochemical properties can be tested by using these as indexes.
The reagent for detecting a tannase high-producing bacterium contained in the diagnostic agent of the present invention is at least one of reagents used for the aforementioned detection of tannase high-producing bacterium and can be suitably selected by those skilled in the art depending on the detection method. Specific examples include a tannin-treated agar medium, bacterium identification kit, primers used for determination of nucleotide sequences by PCR and so forth. The diagnostic agent according to this embodiment can be produced by a technique selected from those usually used for the production of a diagnostic agent depending on the reagent for detecting a tannase high-producing bacterium. When the reagent for detecting a tannase high-producing bacterium is composed of multiple reagents, these reagents may constitute a kit. The reagent for detecting a tannase high-producing bacterium may be used as a composition in combination with a carrier that is acceptable for the use in diagnostic agents.
Components of the diagnostic agent according to this embodiment may include, for example, Brain-Heart Infusion Agar (BHI agar) treated with tannic acid as a selective medium and a bacterium identification kit.
Existence of a tannase high-producing bacterium can be an effective index for the diagnosis or test of colon cancer. That is, presence or absence of colon cancer can be determined based on the detection result for tannase high-producing bacteria in combination with other test results as required. The reason why the existence of the tannase high-producing bacterium can be an effective index for the diagnosis or test of colon cancer is considered that, as shown in the Examples described later, the existence of tannase in a large amount causes colon cancer. Therefore, it is considered that the amount of tannase in the colon can also be an effective index for the diagnosis or test of colon cancer. That is, presence or absence of colon cancer can be determined based on the measurement result for tannase in combination with other test results as required.
Therefore, the present invention also provides a diagnostic agent for colon cancer comprising a reagent for measuring an amount of tannase contained in an intracolonic microflora sample and a test method for colon cancer comprising the step of measuring an amount of tannase in an intracolonic microflora sample.

The amount of tannase may be measured by measuring the enzymatic activity of tannase, or measuring tannase itself by an immunoassay.

The measurement of tannase amount based on the enzymatic activity can be performed by allowing methyl gallate, which is a substrate of tannase, to react with a sample and measuring the amount of the enzymatic reaction product using HPLC or a color development method. For example, the measurement is performed by using methyl gallate as a substrate and quantifying gallic acid as the degrading product by HPLC; mixing methyl gallate and a test specimen and measuring the absorbance at 440 nm; or mixing methyl gallate and a test specimen and observing whether the solution turns to green and then brown color. The quantification is preferably performed based on absorbance.

The measurement of tannase amount by an immunoassay can be performed by a usual immunoassay using an antibody directed to tannase.

Hereafter, an example of a method for producing antibodies directed to tannase and a method for measuring tannase will be explained.

1) Purification of Tannase

Tannase can be purified from a supernatant obtained by culturing a tannase-positive bacterium, disrupting cultured cells by, for example, ultrasonication, and centrifuging the culture. The purification can be performed by a suitable combination of electrophoresis and various chromatography methods (ion exchange chromatography, hydrophobic chromatography, gel filtration etc.) using a tannase activity as an index. The tannase activity can be measured as described above.

2) Production of Antibody

Polyclonal antibodies directed to tannase can be obtained by, for example, immunizing a rabbit or the like with purified tannase. Further, monoclonal antibodies can be obtained by immunizing a mouse or the like and fusing its spleen cell with a myeloma cell.

3) Method for Measuring Tannase in Human Feces

Colon cancer can be diagnosed or tested by measuring tannase contained in an intracolonic microflora sample, for example, feces by immunological techniques using the produced antibodies directed to tannase (anti-tannase antibodies). As the immunoassay, known methods can be employed, and examples thereof include enzyme immunoassay, radioimmunoassay, chemiluminescence immunoassay, electrochemiluminescence immunoassay, immunochromatography, Western blotting, passive particle agglutination, passive hemagglutination, latex particle agglutination and so forth.

An exemplary procedure of the immunoassay is as follows. Anti-tannase antibodies immobilized on a carrier such as a microtiter plate as a solid phase are allowed to react with a specimen sample and, after washing, allowed to react with anti-tannase antibodies labeled with a labeling substance as second antibodies. After washing, the labeling substance is quantified.

As the carrier for immobilizing anti-tannase antibodies on a solid phase, besides the microtiter plate, any of carriers such as magnetosensitive beads, plastic beads, nitrocellulose membrane, nylon membrane, erythrocytes, gelatin particles, polyamino acid particles and latex particles can be used.

In the case of the enzyme immunoassay, an enzyme such as peroxidase, alkaline phosphatase and β-galactosidase is used as the labeling substance of the second antibodies, and the labeling substance is quantified by adding an enzyme substrate and measuring color development of the substrate using a spectrophotometer.

As the labeling substance of the second antibody, besides enzymes, any quantifiable substances such as fluorescent substances, radioactive substances, bioluminescent or chemiluminescent substances, electrochemiluminescent substances, dyes and metals can be used.

In the measurement of the tannase amount in the present invention, absolute values do not necessarily need to be obtained, but it is sufficient to determine whether the values exceed a predetermined value. The predetermined value is a value at which colon cancer is significantly observed.

The reagent for measuring the amount of tannase, which is included in the diagnostic agent of the present invention is at least-one of reagents used for the aforementioned measurement of the amount of tannase and can be suitably selected by those skilled in the art depending on the measurement method. Specific examples thereof include tannase substrates, anti-tannase antibodies and so forth. The diagnostic agent according to this embodiment can be produced by a technique selected from those usually used for the production of a diagnostic agent depending on the reagent for measuring the amount of tannase. When the reagent for measuring the amount of tannase is composed of multiple regents, these reagents may constitute a kit. The reagent for measuring the amount of tannase may be used as a composition in combination with a carrier that is acceptable for the use in diagnostic agents.

Components of the diagnostic agent according to this embodiment may include, in the case of an enzyme immunoassay kit, for example, a plate as a solid phase on which anti-tannase monoclonal antibody is immobilized, enzyme-labeled anti-tannase monoclonal antibody, tannase standard, a specimen-diluting buffer, a washing solution and a reaction-terminating solution.

EXAMPLES

The present invention will be explained more specifically with reference to the following examples. However, the scope of the present invention is not limited to these examples.

Example 1

Isolation of Tannase-Positive Bacterium from Human Feces

1) Collection of Clinical Specimen

Feces collected from 167 in total of patients and healthy subjects who underwent colon endoscopy at Tokyo Medial University Hachioji Medical Center from April, 1999 were used as specimens. Patients in whom colon endoscopy revealed diseases besides colon cancer or polyp of colon in the lower digestive tract were excluded. For colon cancer patients from whom a tannase-positive bacterium was detected, specimens were collected before and after the colon cancer operation. The specimens collected after the operation was collected two weeks after the operation in consideration of influence of antibiotics used during and after the operation.

Each of collected clinical specimens (feces) was inoculated in a Brain-Heart Infusion (BHI) liquid medium (Difco) to which a *Streptococcus* selective supplement (Oxoid) was added, and anaerobically cultured overnight at 37° C. The *Streptococcus* selective supplement was added in an amount of 0.4 ml per 100 ml of the BHI liquid medium.

2) Isolation of Bacterium Having Tannase Activity

Culture for isolation of a bacterium having a tannase activity was performed as follows according to the method of Osawa et al. (Osawa R. et al., Appl. Environ. Microbiol., 56: 829–830, 1990). A *Streptococcus* selective supplement-added tannin-treated BHI agar medium was prepared by the following method.

A BHI agar medium (Oxoid) was autoclaved at 121° C. for 15 minutes, and the *Streptococcus* selective supplement was added to it to prepare a plate agar medium. It was left overnight at 37° C. Subsequently, a PBS buffer to which tannic acid (Kanto Kagaku) was added at 2% (w/v) and sterilized by filtration, was poured over the surface of the plate agar medium left overnight at 37° C. so as to be spread extremely thinly and uniformly and left standing for 20 minutes. After tannic acid and a protein in the medium formed a water-insoluble complex and the surface of the plate agar medium turned white, the tannic acid solution on the surface was removed, and excess tannic acid on the surface of the plate agar medium was washed away with a PBS buffer. The washing was repeated 3 times. After a liquid on the surface was removed, the plate agar medium was left for 1 hour in a substantially vertical state, and then a liquid left at the bottom was removed.

100 µl of clinical specimen cultured in 1) was spread on the prepared *Streptococcus* selective supplement-added tannin-treated BHI agar medium and anaerobically cultured at 37° C. for 3 days. Colonies found to be surrounded by a clear zone were isolated as tannase-positive bacteria.

3) Identification of Isolated Tannase-Positive Bacterium

The tannase-positive bacteria microscopically found to be cocci were identified by using *Staphylococcus* and *Micrococcus* Identification Kit API STAPH (bioMerieux Japan), those found to be streptococci were identified by using Streptococcus Identification Kit AP120 STREP (bioMerieux Japan), and those found to be bacilli were identified by using Lactic acid bacterium identification kit API 50CHL (bioMerieux Japan). Further, as for *S. lugdunensis*, the nucleotide sequence of the 16S-rRNA gene was determined according to the method of Ezaki et al. (Ezaki T. et al., Int. J. Syst. Bacteriol., 44: 130–136, 1994) to confirm homology.

4) Results

Among the fecal specimens collected from the 167 subjects, tannase-positive bacteria were detected from the specimens of 30 subjects. The details of these subjects were 11 (21.6%) of 51 colon cancer patients, 11 (20.4%) of 54 colon polyp patients and 8 (12.9%) of 62 healthy subjects (Table 1). *L. plantarum* was detected in all groups, but *S. lugdunensis* was mostly detected from the colon cancer patients, but detected from only one colon polyp patient. Specimens were collected from the colon cancer patients before and after the colon cancer operation, but no difference was noted between the detection results before and after the operation.

TABLE 1

Isolation of tannase-positive bacteria from colon cancer patients, colon polyp patients and normal subjects

| Patients | Positive | | Negative | Total |
|---|---|---|---|---|
| | S. lugdunensis | L. plantarum | | |
| Colon cancer patients | 9 | 2 | 40 | 51 |
| Colon polyp patients | 1 | 10 | 43 | 54 |
| Normal subjects | 0 | 8 | 54 | 62 |

The nucleotide sequence of the 16S-rRNA gene of isolated *S. lugdunensis* was determined (SEQ ID NO: 1). As a result of the homology search utilizing the database of the DNA Data Bank of JAPAN (DDBJ), this nucleotide sequence showed homology of 99% with the registered 16S-rRNA gene sequence of *S. lugdunensis*.

Example 2

Measurement of Tannase Activity

1) Measurement of Tannase Activity Using HPLC

As a substrate of tannase, methyl gallate (Sigma) having the basic structure of tannic acid was used. Further, as the standard degradation products generated by the degradation of methyl gallate by tannase, gallic acid (Sigma), pyrogallol (Sigma) and phloroglucinol (Sigma) were used. Each of these was prepared at a concentration of 5 mM in 33 mM $NaH_2PO_4$.

Figure 2:
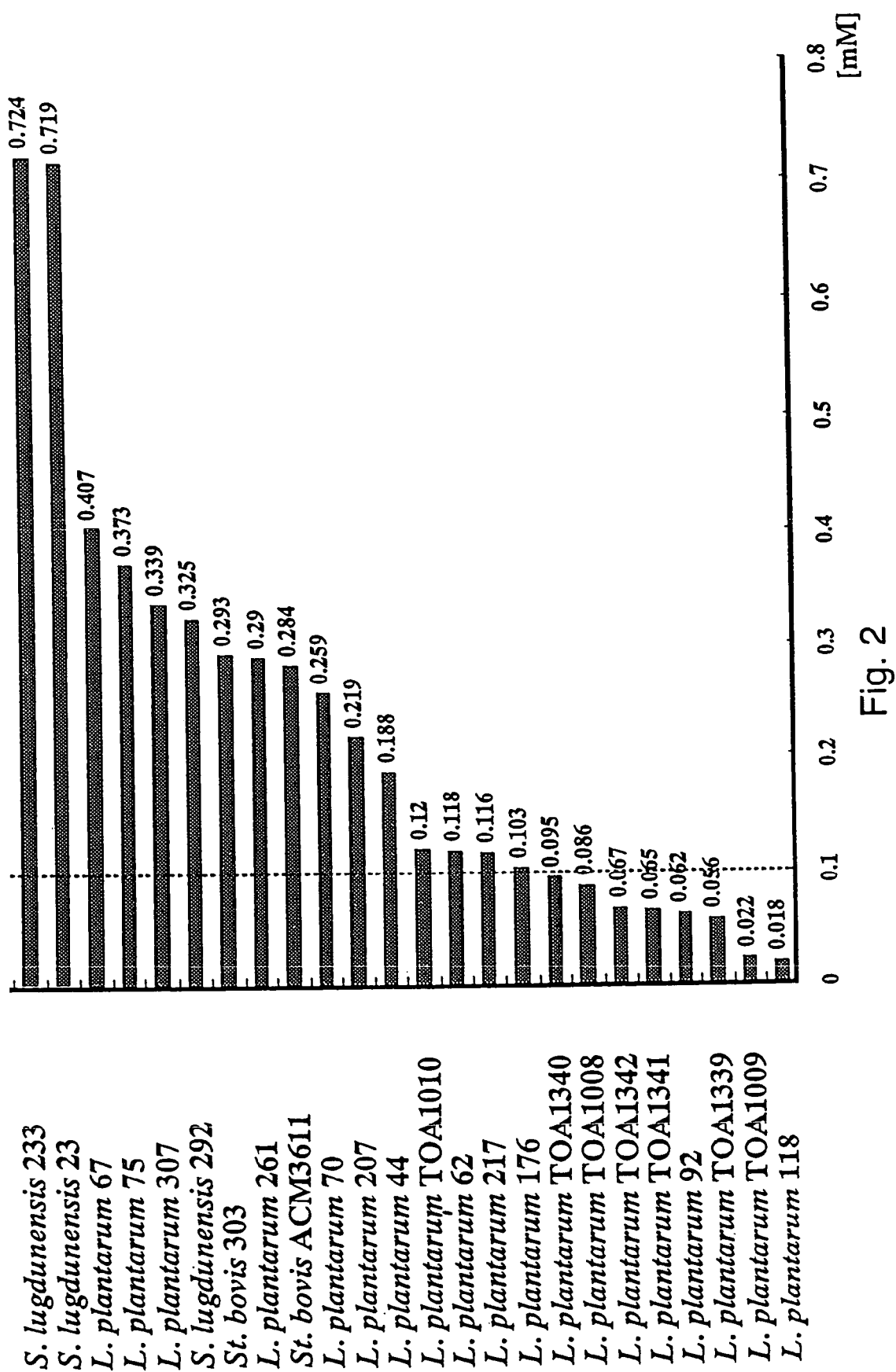
FIG. 2 shows comparison of amounts of tannase produced by St. bovis biotype I, L. plantarum and S. lugdunensis.

The tannase-positive bacteria shown in FIG. 2 were cultured in a tannin-treated BHI agar medium under an anaerobic condition at 37° C. for 72 hours. Then, the bacteria were scraped off with a cotton swab and suspended in 2.5 ml of a substrate solution to prepare a suspension of McFarland turbidity 4, and the suspension was incubated at 37° C. for 24 hours. 1 ml of the incubated suspension was centrifuged at 3,000×g for 1 minute. To 400 µl of the supernatant, an equivalent volume of 0.1 M hydrochloric acid was added and the mixture was further subjected to centrifugal filtration through a membrane filter to obtain a sample solution. Further, as a control, the same pretreatment was performed by using *Escherichia* (*E.*) *coli*.

The decomposition products generated by the decomposition of methyl gallate by tannase were separated and quantified by HPLC. Under the conditions used in this example, retention times of gallic acid, pyrogallol and phloroglucinol were 5.54 minutes, 6.53 minutes and 7.20 minutes, respectively (FIG. 1). Any peak of methyl gallate was not detected.

The total amounts of gallic acid and pyrogallol, which were metabolites produced by the bacteria used in this example from methyl gallate as the substrate were shown in FIG. 2. Among the isolated clinical strains of tannase-positive bacteria, *St. bovis* biotype I, *L. plantarum* and *S. lugdunensis*, it was *S. lugdunensis* that produced the metabolites in the largest amount. As for *E. coli* NIHJ JC-2, no peak was detected for gallic acid and pyrogallol. Any bacteria used in this example did not show a peak for phloroglucinol.

The result that *S. lugdunensis* produced the metabolites in the largest amount among the tannase-positive bacteria and was detected mainly from colon cancer patients indicated the association between the tannase activity and colon cancer. Therefore, it is considered that the existence of tannase high-producing bacteria can be used as an index in tests and diagnoses of colon cancer.

2) Measurement of Tannase Activity by Color Development

Instead of the measurement by HPLC, the tannase activity was also measured by a color development method (performed according to the method of Osawa et al. (Osawa R. et al., Appl. Environ. Microbiol. 59: 1251–1252, 1993)). Methyl gallate (10 mM) dissolved in a phosphate buffer (33 mM $NaH_2PO_4$) and a test specimen were mixed at a ratio of 2:1 and allowed to react at 37° C. for 60 minutes under an aerobic condition. After the reaction, an equivalent volume of a saturated $NaHCO_3$ solution was added to the reaction mixture, and the mixture was left standing at room temperature for 20 minutes, and the absorbance was measured at 440 nm by using a spectrophotometer (DOUBLE-BEAM SPECTROPHOTOMETER UV-190: Shimadzu Corporation). At the same time, the reaction mixture was observed by visual inspection. When the solution turned to green and then brown color, which indicates a high tannase activity, the result was determined to be positive. When the solution was colorless or light yellow, the result was determined to be negative.

Example 3

DNA Damage by Tannin Decomposition Product

After *E. coli* JM109 harboring pBR322 was cultured in an LB medium with shaking, plasmid DNA was extracted by the alkaline method, and the CsCl-ethidium bromide density gradient centrifugation was performed to prepare supercoiled plasmid DNA located in a lower layer.

1 μl of supercoiled plasmid DNA, 1 μl of 1 M phosphate buffer (pH 7.4) and test specimens (methyl gallate, gallic acid and pyrogallol) at concentrations of 0, 0.5, 1, 2.5, 5, 10 and 20 mM were mixed and supplemented with purified water to prepare a reaction mixture of a total volume of 10 μl. Each reaction mixture was incubated at 37° C. for 4 hours, and DNA of a supercoiled form and DNA of a nicked open circular form were separated by agarose gel electrophoresis to determine the activity of the test specimens to damage DNA.

Almost no DNA-damaging ability was observed for methyl gallate, which is a substrate of tannase, but gallic acid and pyrogallol concentration-dependently damaged DNA. Pyrogallol had stronger damaging ability.

These results and the association between the tannase high-producing bacteria and colon cancer support the hypothesis that tannase in a large amount causes colon cancer. Therefore, it is considered that the tannase detection result can also be a useful index in tests and diagnoses of colon cancer.

Example 4

Purification of Tannase

1) Preparation of Crude Enzyme Solution

*L. plantarum* No. 67 was cultured in a tannin-treated BHI agar medium under an anaerobic condition at 37° C. for 3 days (ANAEROBOX AZ series, Hirasawa Seisakusho). One colony was inoculated in 70 ml of BHI medium and cultured with stirring at 37° C. for 18 hours under an anaerobic condition. After the culture, 20 ml of the bacterial solution was added to 1,500 ml of BHI medium and cultured at 37° C. for 24 hours with stirring under an anaerobic condition.

Bacterial cells were collected by centrifuging the culture broth (6,000 rpm, 10 minutes, 4° C.) and suspended in 2.5 ml of 10 mM Tris-HCl (pH 7.5), 10 mM $MgCl_2$, 50 mM NaCl (hereinafter, referred to as M buffer). To the bacterial suspension, 2.5>1 of N-acetylmuramidase SG (Seikagaku Corporation) prepared at 10 mg/ml by using the M buffer was added per ml of the suspension, and the suspension was allowed to react at 37° C. for 30 minutes under an aerobic condition. Further, the bacterial suspension was subjected to ultrasonication and centrifuged (6,000 rpm, 10 minutes, 4° C.), and the centrifugation supernatant was collected to obtain a crude enzyme solution.

2) Fractionation by Ion Exchange Chromatography 25 ml of the crude enzyme solution was applied to DEAE-Sepharose Fast Flow (Pharmacia) packed in Column XK 26/20 (2.6×20 cm: Pharmacia), and unadsorbed substances were eluted with 300 ml of 0.05 M Tris-HCl (pH 7.0) at a flow rate of 5 ml/min. Then, proteins were eluted with a concentration gradient of 0 to 0.4 M NaCl. Further, the remaining proteins were completely eluted with 0.4 M NaCl over 20 minutes. After the elution of the unadsorbed substances, the sample was fractionated into 5-ml fractions. For each fraction, protein content, tannase activity and active oxygen were measured. Fractions showing the activity were lyophilized by using a freeze dryer (FREEZVAC-1: Tozai Tsusho), dissolved in 0.05 M Tris-HCl (pH 7.0) and dialyzed against 0.05 M Tris-HCl (pH 7.0).

3) Fractionation by Gel Filtration Chromatography 2 ml of the fraction having a tannase activity obtained by the ion exchange chromatography was overlaid on Superose 12 (Pharmacia) packed in Column HR 16/50 (1.6×50 cm: Pharmacia). As an elution solution, 0.05 M NaCl, 0.05 M Tris-HCl (pH 7.0) was used. The flow rate was 2 ml/min and the eluate was fractionated into 2-ml fractions. A fraction collector was started 13 minutes after the sample was overlaid on a column. For each fraction, protein content, tannase activity and active oxygen were measured. Fractions showing the activity were collected.

The sample at each purification step was analyzed by SDS-PAGE. As a result, tannase was purified as almost a single band (45 kDa) after the purification using Superose 12.

INDUSTRIAL APPLICABILITY

According to the present invention, diagnosis of colon cancer is enabled based on detection of a tannase high-producing bacterium such as *S. lugdunensis* and/or detection of tannase.

What is claimed is:

1. A test method for colon cancer, which comprises the step of detecting *Staphylococcus lugdunensis* contained in an intracolonic microflora sample.

* * * * *